(12) United States Patent
Hebestreit et al.

(10) Patent No.: US 10,809,245 B2
(45) Date of Patent: Oct. 20, 2020

(54) TEST ELEMENT ANALYSIS SYSTEM FOR THE ANALYTICAL EXAMINATION OF A SAMPLE

(71) Applicant: Roche Diagnostics Operations, Inc., Indianapolis, IN (US)

(72) Inventors: Kai Hebestreit, Heidelberg (DE); Sylvia Saecker, Mannheim (DE); Klaus Thome, St. Leon-Rot (DE); Marina Swan Backhaus, Heidelberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 470 days.

(21) Appl. No.: 15/452,104

(22) Filed: Mar. 7, 2017

(65) Prior Publication Data

US 2017/0261490 A1 Sep. 14, 2017

(30) Foreign Application Priority Data

Mar. 8, 2016 (EP) ..................................... 16159157

(51) Int. Cl.
| | | |
|---|---|---|
| *G01N 33/487* | (2006.01) | |
| *G01N 35/00* | (2006.01) | |
| *B01L 3/00* | (2006.01) | |
| *G01N 21/77* | (2006.01) | |
| *G01N 27/416* | (2006.01) | |

(Continued)

(52) U.S. Cl.
CPC ........ *G01N 33/48792* (2013.01); *B01L 3/545* (2013.01); *G01N 21/77* (2013.01);
(Continued)

(58) Field of Classification Search
CPC ....... G01N 33/48792; G01N 35/00732; G01N 35/00029; G01N 21/77; G01N 27/416;
(Continued)

(56) References Cited

U.S. PATENT DOCUMENTS 6,105,869 A * 8/2000 Scharf ................ G06K 7/10742
 235/454
7,635,834 B2 12/2009 Augstein et al.
(Continued)

FOREIGN PATENT DOCUMENTS

| CN | 201673513 U | 12/2010 |
| CN | 102087215 A | 6/2011 |

(Continued)

OTHER PUBLICATIONS

European Search Report dated Aug. 19, 2016, in Application No. 16159157.3, 8 pages.
(Continued)

*Primary Examiner* — Sally A Merkling
(74) *Attorney, Agent, or Firm* — Roche Diagnostics Operations, Inc.

(57) ABSTRACT

A test element analysis system for the analytical examination of a sample comprising: at least one evaluation device with at least one test element holder and at least one measuring device for measuring a change in a measuring zone of a test element; at least one barcode reader comprising at least one circuit board having a front side facing the barcode of the test element positioned in the test element holder and a reverse side facing away from the test element, wherein at least one electronic control element of the barcode reader is disposed on the circuit board and wherein the circuit board comprises at least one cavity penetrating the circuit board; at least one camera carrier element; and at least one camera electrically connected to the camera carrier element, with the camera carrier element and the camera being positioned such that the camera observes the barcode through the cavity.

15 Claims, 4 Drawing Sheets

(51) Int. Cl.
    *G06K 7/10* (2006.01)
    *G01N 21/84* (2006.01)
(52) U.S. Cl.
    CPC ..... *G01N 27/416* (2013.01); *G01N 35/00029* (2013.01); *G01N 35/00732* (2013.01); *G06K 7/10821* (2013.01); *B01L 2300/021* (2013.01); *B01L 2300/0609* (2013.01); *B01L 2300/0627* (2013.01); *B01L 2300/0654* (2013.01); *G01N 21/8483* (2013.01); *G01N 33/48771* (2013.01); *G01N 2035/00108* (2013.01); *G01N 2035/00752* (2013.01); *G01N 2035/00811* (2013.01); *G06K 7/10861* (2013.01)
(58) Field of Classification Search
    CPC ......... G01N 33/48771; G01N 21/8483; G01N 2035/00752; G01N 2035/00108; G01N 2035/00811; G06K 7/10821; G06K 7/10861; B01L 3/545; B01L 2300/021; B01L 2300/0609; B01L 2300/0627; B01L 2300/0654
    See application file for complete search history.

(56) References Cited

U.S. PATENT DOCUMENTS

| 10,180,400 | B2* | 1/2019 | Hein ................ G01N 21/8483 |
| 2006/0035298 | A1 | 2/2006 | Hill et al. |
| 2008/0180215 | A1 | 7/2008 | Mott |
| 2018/0120586 | A1* | 5/2018 | Kim ................ G02B 27/646 |

FOREIGN PATENT DOCUMENTS

| EP | 1851680 B1 | 12/2010 |
| WO | 2011/076013 A1 | 6/2011 |
| WO | 2012/041967 A1 | 4/2012 |
| WO | 2015/024553 A1 | 2/2015 |

OTHER PUBLICATIONS

Hönes, Joachim et al., The Technology Behind Glucose Meters: Test Strips, Diabetes Technology & Therapeutics, 2008, pp. S-10-S-26, vol. 10, Supplement 1.

* cited by examiner

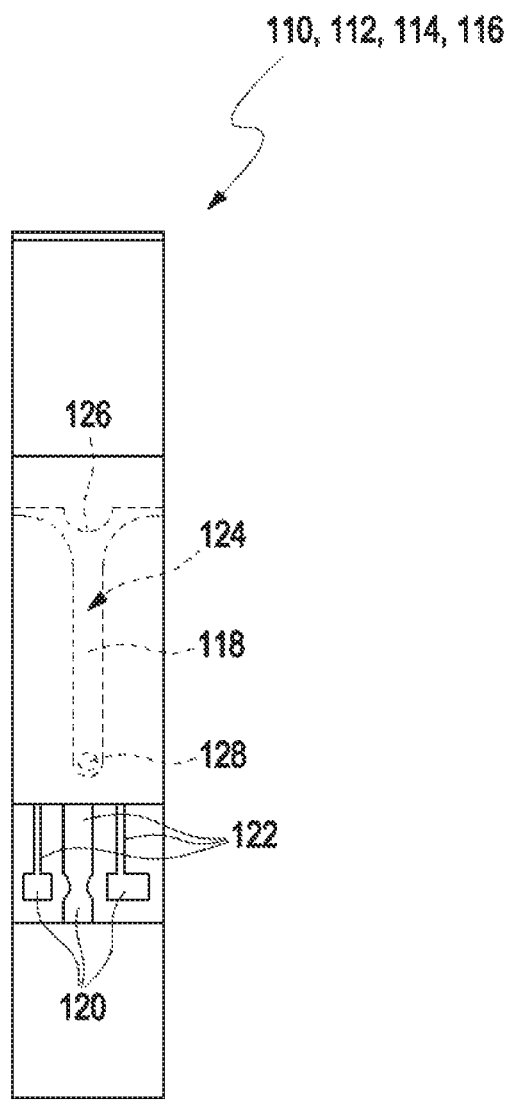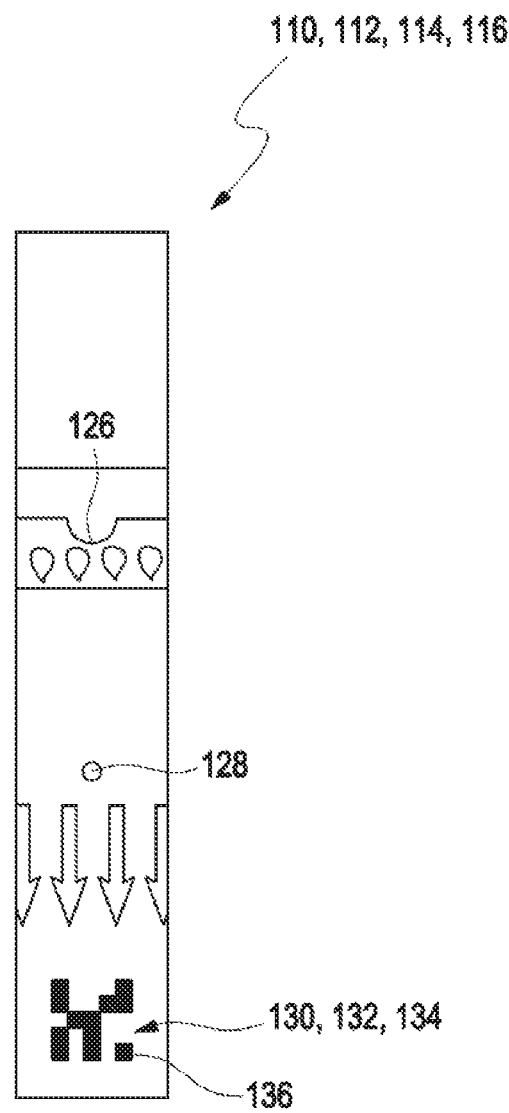

TEST ELEMENT ANALYSIS SYSTEM FOR THE ANALYTICAL EXAMINATION OF A SAMPLE

CROSS-REFERENCE TO RELATED APPLICATIONS

This application claims the benefit of European Patent Application No. 16159157.3, filed Mar. 8, 2016, the disclosure of which is hereby incorporated by reference in its entirety.

BACKGROUND

The present disclosure relates to a test element analysis system for the analytical examination of a sample as well as to a method for manufacturing the same. The devices and methods according to the present disclosure can be used in the field of qualitatively or quantitatively detecting at least one analyte in a sample, such as a sample of a body fluid, and/or for determining at least one parameter of the sample. Other fields of application are feasible.

In the field of medical technology and diagnostics, a large number of devices and methods for determining the presence and/or the concentration of one or more analytes in samples, specifically fluid samples, such as body fluids, are known. Without restricting the scope of the present disclosure, in the following, mainly reference is made to the determination of coagulation parameters in blood or to blood glucose concentrations. It shall be noted, however, that other types of samples or other types of analytes or parameters may be used in a similar way.

For performing fast and simple measurements, several types of test elements are known, which mainly are based on the use of one or more test chemicals, i.e., on the use of one or more chemical substances, one or more chemical compounds or one or more chemical mixtures, adapted for performing a detection reaction for detecting the analyte. The test chemical often is also referred to as a test substance, a test reagent, a test chemistry or as a detector substance. For details of potential test chemicals and test elements comprising such test chemicals, which may also be used within the present disclosure, reference may be made to J. Hoenes et al.: The Technology Behind Glucose Meters: Test Strips, Diabetes Technology & Therapeutics, Vol. 10, Supplement 1, 2008, S-10 to S-26. Other types of test elements and/or test substances are feasible and may be used within the present disclosure.

By using one or more test chemicals, a detection reaction may be initiated, the course of which depends on the presence and/or the concentration of the at least one analyte to be determined. The detection reaction typically may be analyte-specific. Typically, as may also be the case in the present disclosure, the test chemical is adapted to perform at least one detection reaction when the analyte is present in the body fluid, wherein the extent and/or the degree of the detection reaction typically depends on the concentration of the analyte. Generally, the test chemical may be adapted to perform a detection reaction in the presence of the analyte, wherein at least one detectable property of at least one of the body fluid and the test chemical is changed due to the detection reaction. The at least one detectable property generally may be selected from a physical property and a chemical property.

In the following, without restricting potential other embodiments, reference will mainly be made to detection reactions in which one or more physical properties are changed due to the detection reaction, such as one or more of at least one electrical property and at least one optical property. Further, without restricting alternative solutions, reference will be made to detection reactions in which at least one chemical property that is electrically detectable is changed, i.e., to electrochemical test elements. Other test elements, such as optical test elements, however, are usable, too.

In the technical field of analytical devices, the use of barcodes and barcode readers is possible, such as for providing information on the specific details of the test element in use to the test element analysis system. Thereby, as an example, lot-specific data, expiry date, calibration parameters or other information on the test element may be transferred to the analysis system.

Despite the advantages of known devices and methods, several technical challenges remain. Thus, specifically for hand-held devices, the volume of the barcode reader and the height of the overall optical system still is an issue. This is mainly due to the fact that typical barcodes extend over at least several millimeters on the test element. In order to read barcodes of said lateral dimensions, even though wide-angle cameras may be used, still, the free working distance between the barcode and the barcode reader is rather significant, which has to be taken into account as an additional space and volume for the analytical system.

It is therefore an objective of the present disclosure to provide devices and methods that at least partially overcome the above-identified technical challenges.

SUMMARY

It is against that above background that the present disclosure provides certain unobvious advantages and advancements over the prior art. In particular, the inventors have recognized a need for improvements in test element analysis systems for the analytical examination of a sample and a method for manufacturing the same.

Although the present disclosure is not limited to specific advantages or functionality, it is noted that the present disclosure provides a test element analysis system that allows for a small volume and a reduction of the working space as compared to conventional analytical devices having a barcode reader.

In accordance with one embodiment of the present disclosure, a test element analysis system for the analytical examination of a sample is provided comprising: at least one evaluation device with at least one test element holder for positioning at least one test element containing the sample and at least one measuring device for measuring a change in a measuring zone of the test element, the change being characteristic for an analyte or a parameter of the sample. The system further comprises at least one barcode reader for reading at least one barcode on the test element, wherein the barcode reader comprises: at least one circuit board, the circuit board having a front side facing the barcode of the test element positioned in the test element holder and at least one reverse side facing away from the test element, wherein at least one electronic control element of the barcode reader is disposed on the circuit board, and wherein the circuit board comprises at least one cavity penetrating the circuit board; at least one camera carrier element being disposed on the reverse side of the circuit board; and at least one camera. The camera is electrically connected to the camera carrier element, with the camera carrier element and the camera being positioned such that the camera observes the barcode through the cavity.

These and other features and advantages of the embodiments of the present disclosure will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which:

FIG. 1A shows an exemplary embodiment of a test element in a back view;

FIG. 1B shows an exemplary embodiment of a test element in a front view;

Figure 2:
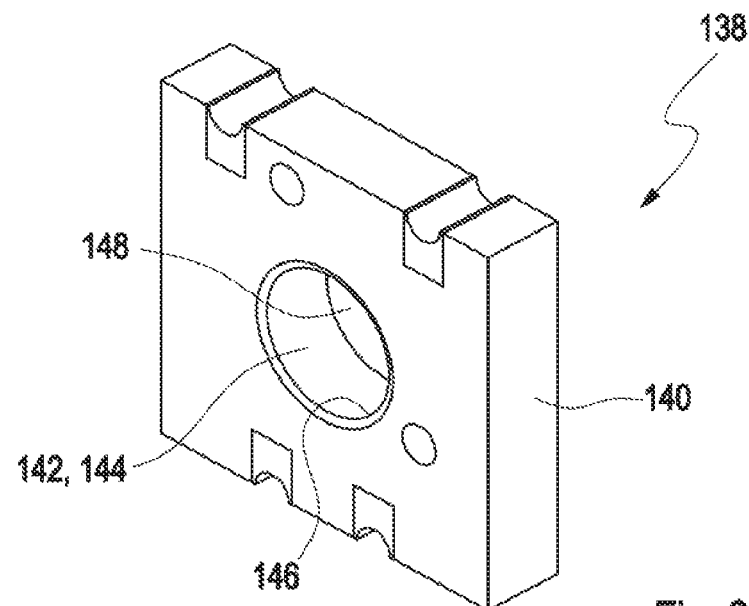
FIG. 2A shows an exemplary embodiment of a camera carrier element in a perspective view.
FIG. 2B shows an exemplary embodiment of a camera carrier element in a front view.
Figure 2:
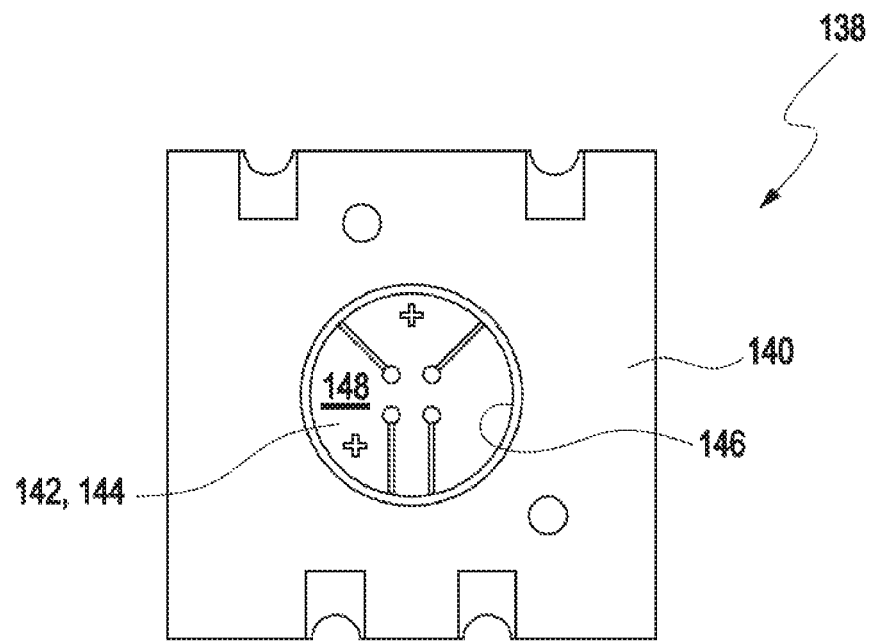

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present disclosure.

DETAILED DESCRIPTION

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, notwithstanding the fact that the respective feature or element may be present once or more than once.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention," "in an embodiment of the disclosure," or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect of the present disclosure, a test element analysis system for the analytical examination of a sample, in particular of a body fluid, is disclosed. The test element analysis system comprises at least one evaluation device with at least one test element holder for positioning at least one test element containing the sample. Further, the evaluation device comprises at least one measuring device for measuring a change in a measuring zone of the test element. The change is characteristic for an analyte or a parameter of the sample. Further, the test element analysis system comprises at least one barcode reader for reading at least one barcode on the test element. The barcode reader comprises at least one circuit board. The circuit board has a front side facing the barcode of the test element positioned in the test element holder. Further, the circuit board has at least one reverse side facing away from the test element. At least one electronic control element of the barcode reader is disposed on the circuit board. The circuit board comprises at least one cavity, which at least partially or fully penetrates the circuit board. The barcode reader further comprises at least one camera carrier element being disposed on the reverse side of the circuit board and at least one camera. The camera is electrically connected to the camera carrier element, with the camera carrier element and the camera being positioned such that the camera observes the barcode through the cavity of the circuit board.

As further used herein, the term "system" refers to an arbitrary set of interacting or interdependent components parts forming a whole. Specifically, the components may interact with each other in order to fulfill at least one common function. The at least two components may be handled independently or may be coupled or connectable. Thus, the term "test element analysis system" generally refers to a group of at least two elements or components which are capable of interacting in order to perform at least one analytical detection by interacting with an arbitrary test element, specifically at least one analytical detection of at least one analyte of the sample. The test element analysis system may generally also be referred to as an analytical system, an analytical kit, a sensor system or a measurement system.

As generally used within the present disclosure, the terms "patient" and "user" may refer to a human being or an animal, independent from the fact that the human being or animal, respectively, may be in a healthy condition or may suffer from one or more diseases. As an example, the patient or the user may be a human being or an animal suffering from diabetes. However, additionally or alternatively, the disclosure may be applied to other types of users or patients or diseases.

As further used herein the term "sample" may refer to an arbitrary material or combination of materials taken for an analysis, testing or investigation. The sample may be a limited quantity of something which is intended to be similar to and represent a larger amount. However, the sample may also comprise a full specimen. The sample may be solid sample, a liquid sample or a gaseous sample or a combination of these. Specifically, the sample may be a fluid sample, i.e., a sample which fully or partially is in a liquid state and/or in a gaseous state. A quantity of the sample may be describable in terms of its volume, mass or size. However, other dimensions are feasible. The sample may comprise only one material or only one compound. Alternatively, the sample may comprise several materials or compounds.

The term "analyte" generally refers to an arbitrary element, component or compound which may be present in the sample and the presence and/or the concentration of which may be of interest for the user, the patient or medical staff such as a medical doctor. Particularly, the analyte may be or may comprise an arbitrary chemical substance or chemical compound which may take part in the metabolism of the user or the patient, such as at least one metabolite. The detection of the at least one analyte specifically may be an analyte-specific detection.

The term "parameter" generally may refer to an arbitrary value such as a measurement value which is obtainable within or by an analytical test. Exemplarily, the parameter may correspond to a property of the sample and/or a property of the at least one analyte as described above. Specifically, the parameter may be a coagulation parameter such as to a coagulation time of the analyte. For further details on the term "coagulation parameter" as further used herein, reference may be made to US 2006/0035298.

As further used herein, the term "body fluid" may refer to a fluid which typically is present in a body or body tissue of the user or the patient and/or which may be produced by the body of the user or the patient. As an example for body tissue, interstitial tissue may be named. Thus, as an example, the body fluid may be selected from the group consisting of blood and interstitial fluid. However, additionally or alternatively, one or more other types of body fluids may be used, such as saliva, tear fluid, urine or other body fluids. During detection of the at least one analyte, the body fluid may be present within the body or body tissue. Thus, specifically, as will be outlined in further detail below, the sensor may be configured for detecting at least one analyte in a body tissue.

The term "analytical examination" generally may refer to a process of determining the presence and/or the quantity and/or the concentration of the at least one analyte or to a process of determining a parameter of the sample that is characteristic of the properties of the sample, e.g., a coagulation parameter that is characteristic of the coagulation properties of a blood sample. The detection may be or may comprise a qualitative detection, simply determining the presence of the at least one analyte or the absence of the at least one analyte, and/or may be or may comprise a quantitative detection, which determines the quantity and/or the concentration of the at least one analyte. As a result of the detection, at least one signal may be produced which characterizes an outcome of the detection, such as at least one measurement signal. The at least one measurement signal specifically may be or may comprise at least one electronic signal such as at least one voltage and/or at least one current. The at least one signal may be or may comprise at least one analogue signal and/or may be or may comprise at least one digital signal.

The term "test element" generally may refer to an arbitrary device which is capable of detecting the analyte in the sample or of determining the parameter of the sample. The test element may specifically be a strip-shaped test element. As used herein, the term "strip-shaped" refers to an element having an elongated shape and a thickness, wherein an extension of the element in a lateral dimension exceeds the thickness of the element, such as by at least a factor of 2, typically by at least a factor of 5, more typically by at least a factor of 10 and most typically by at least a factor of 20 or even at least a factor of 30. Thus, the test element may also be referred to as test strip.

The test element may comprise at least one component or at least one reagent which changes at least one detectable property when the analyte is present in the sample such as a test chemistry. The term "test chemistry", also referred to as a test chemical, may refer to an arbitrary material or a composition of materials adapted to change at least one detectable property in the presence of the analyte. Generally, this property may be selected from an electrochemically detectable property and/or an optically detectable property, such as a color change and/or a change in remissive properties. Specifically, the test chemistry may be a highly selective test chemistry, which only changes the property if the analyte is present in the sample of the body fluid applied to the test element, whereas no change occurs if the analyte is not present. More typically, the degree or change of the property may be dependent on the concentration of the analyte in the body fluid, in order to allow for a quantitative detection of the analyte.

Specifically, the test element may comprise at least one reagent configured for activating a coagulation of components of the body fluid. The reagent may comprise reactive components of thromboplastin and a peptide substrate. Thus, in case the reagent is exposed to the sample, the thromboplastin may activate a clotting and thrombin may be generated. Thrombin may cleave the peptide substrate and an electrochemical signal may be generated. The electrochemical signal may be evaluated with regard to a time of its occurrence. However, other reagents and/or measurement principles may be feasible.

As used herein, the term "electrochemical detection" refers to a detection of an electrochemically detectable property of the analyte by electrochemical means, such as an electrochemical detection reaction. Thus, for example, the electrochemical detection reaction may be detected by comparing one or more electrode potentials, such as a potential of a working electrode with the potential of one or more further electrodes such as a counter electrode or a reference electrode. The detection may be analyte specific. The detection may be a qualitative and/or a quantitative detection.

The test element may have the at least one measuring zone capable of performing at least one change being characteristic for the analyte or the parameter. As further used herein, the term "measuring zone" may refer to an arbitrary area or region of an object wherein an arbitrary measurement, specifically an analytical measurement, is conducted. Specifically, the test chemistry as described above may be located within the measuring zone, particularly on a surface of the measuring zone.

The test element may be an electrochemical test element. The term "electrochemical test element" may refer to an arbitrary test element configured for conducting at least one electrochemically detection. As used herein, the term "electrochemically detection" refers to a detection of an electrochemically detectable property of at least one arbitrary analyte, such as an electrochemical detection reaction. Thus, for example, the electrochemical detection reaction may be detected by comparing one or more electrode potentials, such as an electrostatic potential of a working electrode with the electrostatic potential of one or more further electrodes such as a counter electrode or a reference electrode. The detection may be analyte specific. The detection may be a qualitative and/or a quantitative detection.

The test element may comprise at least one capillary configured for receiving the sample. The term "capillary" generally refers to an arbitrary small, elongate void volume such as a small tube. Generally, the capillary may comprise dimensions in the millimeter or sub-millimeter range. Commonly, a fluidic medium may migrate through the capillary by capillary action wherein the fluidic medium may flow in narrow spaces of the capillary without an assistance of external forces like gravity due to intermolecular forces between the fluidic medium and a surface of the capillary facing the fluidic medium.

The test element may further comprise the at least one barcode. As further used herein, the term "barcode" may refer to an arbitrary information carrier which is configured to be read out by optical or optoelectronic means and which may have a plurality of optically detectable modules which each may assume at least two different optically detectable states. Specifically, the barcode may carry at least one optical item of information selected from the group consisting of: a type of test; a batch or lot number; a manufacturing date; an expiration date; and an item of information about a calibration. Still, other optical information is feasible.

The term "module" may generally refer to a two-dimensional or three-dimensional region of the barcode. Specifically, the modules may be or may comprise defined two-dimensional regions on a surface of a carrier of the barcode, or else to three-dimensional regions within a material of the carrier. The modules may specifically be the smallest unit of information of the barcode.

Important examples, to which, however, the application is not restricted, are so-called linear codes or line codes, i.e., one-dimensional barcodes in which the modules comprise a sequence of rows which may assume at least two different values (e.g., "white" and "black"). As an alternative or in addition thereto, use may also be made of two-dimensional barcodes, for example so-called data matrix codes, in which modules are applied in two directions and for example arranged to form a matrix. In this case, the modules may, for example, be embodied as squares or rectangles. However, in principle, other embodiments may also be feasible. In respect of possible barcodes, reference may be made, for example, to conventional commercial barcodes according to the EAN (European Article Number), UPC (Universal Product Code) or similar codes. Other known standards for barcodes are also applicable. In respect of two-dimensional barcodes, reference may be made, for example, to data matrix codes, QR codes, codes according to the PDF standard or similar codes.

The barcode may specifically be a binary barcode comprising the at least two different optically detectable states. In the case of binary barcodes, the at least two states may be binary, i.e., a first state or a second state may be assumed. However, in principle, other embodiments may also be feasible, i.e., embodiments in which more than two states may be feasible, which, for example, may be realized within the scope of so-called grayscale codes.

Optically perceivable properties which may assume the at least two states may be one of different types of optical properties. Exemplarily, this may be a reflectivity, a color, fluorescence, transparency or another type of optical properties or a combination of the aforementioned and/or other properties. The optically perceivable property may for example be directly introduced into the carrier of the barcode, for example into a material and/or onto a surface of the carrier, or may, as an additional marking material, for example be applied to the carrier. Exemplarily, reference may be made to printing a color onto a surface of the carrier, as a result of which, e.g., the reflectivity and/or the transparency of the carrier surface and/or a fluorescent property of the carrier surface are changed. Exemplarily, this additional marking material may be printed, sprayed or dripped onto the carrier or else applied to the carrier by means of a separate carrier element, e.g., an adhesive film. Alternatively, it may also be feasible to modify the carrier itself, for example by irradiation, for example by means of a laser, by means of which the barcode is applied onto or introduced into the carrier directly or, in turn, onto or into a marking material connected to the carrier. Various embodiments may be feasible.

The term "barcode reader" may generally refer to an arbitrary device which is configured to read out the barcode at least to the extent that the information from the barcode is converted into electric signals or storage states of a data storage of the barcode reader. Therefore, the barcode reader may comprise at least one device with an optical emitter for emitting at least one kind of electromagnetic radiation, typically light in the visible and/or infrared and/or ultraviolet spectral range. The device may thus also be referred to as light source.

Further, the barcode reader comprises the at least one camera. As further used herein, the term "camera" may refer to an arbitrary optical instrument configured for receiving electromagnetic radiation, typically light in the infrared and/or visible and/or ultraviolet spectral range. Thus, the camera may be configured for recording images, which may be stored locally, transmitted to another location or both. The camera may also be referred to as detector or optical detector.

Specifically, the term "camera" may relate to an arbitrary device which is configured to capture the properties of the modules of the barcode, which may assume the at least two states, in a qualitative or typically quantitative fashion. The camera may be configured for at least one-dimensional capture of modules of the barcode. As further used herein, the term "capture of information modules" of the barcode may generally refer to a property of the camera of recording information in a temporal sequence, specifically in case of movement of the barcode relative to the barcode reader.

The camera may be an integrated chip comprising one or more of a CCD or a CMOS camera. Specifically, the camera may comprise at least one optically sensitive element, for example a photodiode, a photocell, a CCD chip, a phototransistor or similar optically sensitive elements which may be configured to detect an intensity or changes in an intensity of incident electromagnetic radiation, more particularly of light in the visible and/or infrared and/or ultraviolet spectral range. The term "charge-couple device (CCD) camera" may generally refer to an arbitrary device which comprises an array of a large number, specifically of at least one hundred, of small light sensors lined up in a row. Each light sensor may be configured to measure an intensity of light. The CCD camera may be configured to generate at least one voltage pattern identical to a pattern of an object which shall be depicted, specifically by sequentially measuring the voltages across each light sensor in the row. The term "complementary metal-oxide-semiconductor (CMOS) camera" may generally refer to an arbitrary device which comprises an array of pixel sensors, specifically of photodetectors, and an active amplifier. Thereby, the CMOS camera may be produced by a complementary metal-oxide-semiconductor technology. Beyond, the integrated camera chip may comprise one or more of a lens system or an aperture system. The term "lens" may refer to an arbitrary transmissive optical device which is configured to affect a focus of a light beam through refraction and the term "aperture" may generally refer to an arbitrary hole or opening through which light travels.

The term "circuit board" may generally refer to an arbitrary device which is configured to mechanically support and/or to electrically connect electronic components, specifically by using tracks, pads and/or other elements such as transistors or resistors. The circuit board may specifically be a printed circuit board. The term "printed circuit board" may generally refer to an arbitrary circuit board wherein the tracks, pads and/or the other components may be etched from copper sheets laminated onto a non-conductive substrate. The substrate may exemplarily be made of at least one of fiberglass, composite epoxy, a laminate material. As described above, the at least one electronic control element of the barcode reader is disposed on the circuit board.

The term "electronic control element" may generally refer to an arbitrary electronic device which is configured to control one or more electrical systems or subsystems. Specifically, the electronic control element may comprise at least one electronic component which is configured for one or more of driving, monitoring or evaluating a barcode reading function. The barcode evaluation device may be configured for controlling a barcode reading and/or for one or more of recording, storing, evaluating, monitoring of optical information provided by the camera. Specifically, the barcode evaluation device may be configured to derive at least one item of information from the barcode. The barcode evaluation device may comprise software and/or hardware components. Further, the electronic control element may comprise at least one data processing device, optionally with one or more volatile or non-volatile storage elements. Moreover, the electronic control element may comprise one or more operating elements such as entering commands and/or control data and/or other information. Further, the electronic control element may comprise one or more display devices and/or other types of user interfaces. The electronic control element may be embodied as a single component or may be embodied as a number of parts, optionally also distributed over various regions of the circuit board. The control element may comprise one or more of a processor, an FPGA, a DSP, or an ASIC. Other embodiments are feasible.

As described above, the circuit board has the front side and the reverse side. The term "side" may generally refer to an arbitrary component or part of an object which may be viewable from one perspective. In case the object has the shape of a cuboid, the term "side" may specifically refer to one surface of the cuboid. The terms "front side" and "reverse side" may be considered as description without specifying an order and without excluding a possibility that several kinds of front sides and reverse sides faces may be applied.

As described above, the circuit board comprises the at least one cavity penetrating the circuit board. The term "cavity" may generally refer to an arbitrary void volume within a surface of a solid material. Specifically, the cavity may be a through-hole in the circuit board. Optionally, the through-hole may be covered with a layer, specifically with a transparent layer. The layer may cover the through-hole on one side of the circuit board, specifically on the reverse side of the circuit board. Further, the cavity may have at least one cross-section selected from the group consisting of: a round cross-section, an oval cross-section, a polygonal cross-section and, particularly, a rectangular cross-section.

The term "carrier element" may generally refer to an arbitrary object which is configured to hold, support or to receive another element. The other element may lie slackly on the object or may be firmly attached to the object. Exemplarily, the other element may be bonded onto the object or may be integrated into the object. The term "bonded" may generally refer to a property of an arbitrary element of being fixedly connected to another object. Specifically, the element may be connected to the object via at least one adhesive material or via soldering. However, other embodiments may be feasible.

The term "integrated" may refer to a state wherein two or more objects may be permanently built into at least another one of the two or more objects. Thus, the two or more objects may form a single piece. Thus, the two or more objects may be arranged in a space-saving or compact manner. Further, the two or more objects may be designed in a complementary manner such that the components may be able to interact with each other. Exemplarily, the camera carrier element may be one of bonded onto the reverse side of the circuit board or may be integrated into the reverse side of the circuit board and/or connected to the reverse side of the circuit board via at least one plug connection. Specifically, the circuit board and the camera carrier element may be printed circuit boards and the printed circuit board of the camera carrier element may be bonded on the reverse side of the circuit board.

The term "evaluation device" may generally refer to an arbitrary device being configured to derive at least one item of information from data. Specifically the evaluation device may be configured to derive the at least one item of information regarding the presence and/or concentration of the analyte in the body fluid or a parameter of the body fluid from at least one signal.

As described above, the evaluation device comprises the measuring device. The term "measuring device" generally may refer to an arbitrary device, typically an electronic device, which may be configured to detect at least one signal. The signal may be an optical signal and/or an electrochemical signal. The measuring device may be handled independently from the test element and may be adapted to interact with the test element in order to perform an analysis, such as by detecting the at least one signal. Thus, the term "measuring device" may often also be referred to as a measurement device, an analytical device, a meter or a test device.

As described above, the evaluation device comprises the test element holder. The term "test element holder" generally may refer to an arbitrary object which is configured to receive or to hold an arbitrary test element. Specifically, the test element may be positioned on a specific position within the test element holder such that a movement of the test element in at least one direction may be suppressed at least to a large extent. Thus, the measurement zone and/or the barcode of the test element may be located in a predetermined position relative to the measuring device and the camera, respectively. The test element may specifically be configured to be put reversibly into the test element holder. Thus, the test element may be removable from the test element holder without further ado. Still, other embodiments are feasible. The test element may be at least partially received in the test element holder. The term "being received" may generally refer to a condition of an object being located or inserted fully or at least partially into a receptacle or into an opening of another element. Thus, a part of the object may be located outside of the other element. Exemplarily, the test element holder may comprise at least one receptacle configured for receiving the test element. Thus, the receptacle may be shaped complementary to the test element. Therefore, the receptacle and the test element may be configured to establish a form-fit connection. The barcode reader and the measuring device may be located on opposing sides of the receptacle. Still, other embodiments are feasible. The test element holder may comprise at least one contact element with contact surfaces which allow an electrical contact between contact surfaces of the test element and the contact surfaces of the test element holder.

The camera carrier element may comprise electrical contacts electrically connected to the camera. Thereby, the electrical contacts may be electrically connected to at least one electrical contact of the circuit board. The electrical contact of the circuit board may be located on the reverse side of the circuit board. The circuit board may comprise at least one via electrically connecting the electrical contact of the circuit board located on the reverse side with the at least one electronic control element located on the front side. As used herein, the term "contact element" generally refers to an arbitrary element which is electrically conductive. Further, the contact element may comprise one or more surfaces, specifically flat surfaces, which may be configured to establish a close connection to other electrically conductive elements. The term "via" may generally refer to an arbitrary electrical connection between layers which go through at least one plane of one or more adjacent layers.

The camera carrier element may comprise at least one printed circuit board having at least one electrical contact pad with the camera electrically bonded thereon. As used herein, the term "contact pad" generally refers to an element having an open or electrically contactable surface which is electrically conductive. As an example, the contact pads may be or may comprise at least one layer of at least one electrically conductive material which directly or indirectly may be deposited onto the substrate and which provides an electrically contactable surface. In a dimension or direction parallel to a surface of the substrate, the contact pads may provide a contact surface area, such as an area having a rectangular shape, a polygonal shape or a round shape. Other shapes are possible.

The camera carrier element may comprise a camera carrier element cavity. The camera carrier element may be positioned such that the camera carrier element cavity is fully or partially located inside the cavity or in an overlapping fashion with the cavity of the circuit board. The camera may be mounted inside the camera carrier element cavity. Specifically, the camera carrier element cavity may be a blind hole with an opening facing the test element. The camera carrier element may comprise at least one electrical contact pad inside the camera carrier element cavity and the camera may be electrically bonded onto the electrical contact pad.

The camera may comprise a front face. The term "face" as further used herein may refer to part of an object which may be viewable from one perspective. Specifically, the front face of the camera may refer to a part of the camera which is configured for recording the images. Thereby, the term "front face" and may be considered as description without specifying an order and without excluding a possibility that several kinds of front faces may be existent. A distance between the barcode of the test element inside the test element holder and the front side of the circuit board may be smaller or less than a distance between the barcode and the front face of the camera. Specifically, the distance between the barcode and the front side of the camera may exceed the distance between the barcode and the front side of the circuit board by at least the thickness of the circuit board. As further used herein, the term "distance" may refer to a numerical description of how far apart two or more objects are from each other. Specifically, the distance may refer to a physical length. The term "thickness" may generally refer to a dimension of an arbitrary object perpendicular to a direction of extension of an object. Specifically, the circuit board may have an elongate shape and the front side may refer to a side of the circuit board which extends along the direction of extension. Thereby, the thickness may refer to a dimension of the circuit board perpendicular to the front side of the circuit board. Specifically, the thickness of the circuit board may contribute to a free working distance of the camera. The term "free working distance" may refer to a distance between an arbitrary camera, specifically a front lens of the camera, and an arbitrary focused object.

In a further aspect of the present disclosure, a method for manufacturing the test element analysis system according to any embodiment as described above or as further described below is disclosed. The method steps may be performed in the given order. However, other orders of the method steps are feasible. Further, one or more of the method steps may be performed in parallel and/or on a timely overlapping fashion. Further, one or more of the method steps may be performed repeatedly. Further, additional method steps may be present which are not listed.

The method for manufacturing the test element analysis system comprises:
- a) providing the circuit board;
- b) providing the camera carrier element;
- c) connecting the camera to the camera carrier element;
- d) connecting the camera carrier element to the reverse side of the circuit board.

In step c), the camera may be connected to the camera carrier element by bonding. Specifically, the camera carrier element may be bonded to the reverse side of the circuit board. Additionally or alternatively, the carrier element and the circuit board may be manufactured as one single piece.

The proposed test element analysis system for the analytical examination of a sample as well as the proposed method for manufacturing the test element analysis system provide many advantages over known devices and methods.

Generally, a construction height of components, specifically in the field of hand held medical devices such as hand held analysis systems, remains challenging. As not only the construction height of the elements of the optical system themselves but also the free working distance contributes to a required total construction height of cameras or camera systems, this aspect may specifically have to be considered.

Usually, common test element analysis systems generally may comprise large installation spaces, large free working distances and/or may be high priced. Generally in case of small installation spaces there may be a long focal length which may specifically lead to a large free working distance. Moreover, construction units may generally only be available in the short term (consumer market).

Therefore, the test element analysis system according to the present disclosure may comprise the camera which is placed into the carrier element cavity of the carrier element and may exemplarily be soldered to the carrier element and/or may be sealed. This unit may be soldered to the reverse side of the circuit board with the camera looking down, i.e., towards the cavity of the circuit board. The camera may face a plane to be detected through the cavity of the circuit board. Therefore, the thickness of the circuit board may contribute to the free working distance.

In a further aspect, a barcode reader for reading at least one barcode is disclosed. The barcode reader comprises:
at least one circuit board, the circuit board having a front side facing the barcode and at least one reverse side facing away from the barcode, wherein at least one electronic control element of the barcode reader is disposed on the circuit board and wherein the circuit board comprises at least one cavity penetrating the circuit board;

at least one camera carrier element being disposed on the reverse side of the circuit board;

at least one camera, the camera being electrically connected to the camera carrier element, with the camera carrier element and the camera being positioned such that the camera observes the barcode through the cavity.

For definitions of the features of the barcode reader and for optional details of the barcode reader, reference may be made to one or more of the embodiments of the test element analysis system as disclosed above or as disclosed in further detail below. Specifically, the barcode reader may be embodied having the features referring to the barcode reader according to one or more of the embodiments of the test element analysis system.

Advantages of the test element analysis system according to the present disclosure may be a low construction height, specifically as the camera may be placed within the camera carrier element.

Moreover, the camera may be protected from mechanical stress and may be shielded against environmental influences such as moisture and/or ambient atmosphere, electromagnetic influences or the like. The protection may specifically be achieved by placing the camera within the camera carrier element and/or by sealing the camera, specifically by sealing the camera carrier element cavity. Further, the free working distance may be increased, specifically as the camera may be configured to look through the cavity of the circuit board. Exemplarily, the cavity may be integrated into the camera carrier element. Eventually, this may lead to a lower free working distance which may be compensated by a higher thickness of the circuit board.

Summarizing the findings of the present disclosure, the following embodiments are typical:

Embodiment 1

A test element analysis system for the analytical examination of a sample, in particular of a body fluid, comprising:
- at least one evaluation device with at least one test element holder for positioning at least one test element containing the sample and at least one measuring device for measuring a change in a measuring zone of the test element, the change being characteristic for an analyte or a parameter of the sample;
- at least one barcode reader for reading at least one barcode on the test element, wherein the barcode reader comprises:
  - at least one circuit board, the circuit board having a front side facing the barcode of the test element positioned in the test element holder and at least one reverse side facing away from the test element, wherein at least one electronic control element of the barcode reader is disposed on the circuit board and wherein the circuit board comprises at least one cavity penetrating the circuit board;
  - at least one camera carrier element being disposed on the reverse side of the circuit board;
  - at least one camera, the camera being electrically connected to the camera carrier element, with the camera carrier element and the camera being positioned such that the camera observes the barcode through the cavity.

Embodiment 2

The test element analysis system according to the preceding embodiment, wherein the camera carrier element is one of bonded onto the reverse side of the circuit board, integrated into the reverse side of the circuit board or connected to the reverse side of the circuit board via at least one plug connection.

Embodiment 3

The test element analysis system according to any one of the preceding embodiments, wherein the camera carrier element comprises at least one printed circuit board having at least one electrical contact pad with the camera electrically bonded thereon.

Embodiment 4

The test element analysis system according to any one of the preceding embodiments, wherein the circuit board and the camera carrier element are printed circuit boards, wherein the printed circuit board of the camera carrier element is bonded on the reverse side of the circuit board.

Embodiment 5

The test element analysis system according to any one of the preceding embodiments, wherein the cavity is a through-hole in the circuit board.

Embodiment 6

The test element analysis system according to any one of the preceding embodiments, wherein the camera carrier element comprises a camera carrier element cavity, wherein the camera carrier element is positioned such that the camera carrier element cavity is fully or partially located inside the cavity or in an overlapping fashion with the cavity of the circuit board, wherein the camera is mounted inside the camera carrier element cavity.

Embodiment 7

The test element analysis system according to the preceding embodiment, wherein the camera carrier element cavity is a blind hole with an opening facing the test element.

Embodiment 8

The test element analysis system according to any one of the two preceding embodiments, wherein the camera carrier element comprises at least one electrical contact pad inside the camera carrier element cavity, with the camera is electrically bonded onto the electrical contact pad.

Embodiment 9

The test element analysis system according to any one of the preceding embodiments, wherein the camera comprises a front face, wherein a distance between the barcode of the test element when placed inside the test element holder and the front side of the circuit board is smaller or less than a distance between the barcode and the front face of the camera.

Embodiment 10

The test element analysis system according to the preceding embodiment, wherein the distance between the barcode and the front face of the camera exceeds the distance between the barcode and the front side of the circuit board by at least the thickness of the circuit board.

Embodiment 11

The test element analysis system according to the preceding embodiment, wherein the thickness of the circuit board contributes to a free working distance of the camera.

Embodiment 12

The test element analysis system according to any one of the preceding embodiments, wherein the test element holder contains contact elements with contact surfaces which allow an electrical contact between contact surfaces of the test element and the contact surfaces of the test element holder.

Embodiment 13

The test element analysis system according to any one of the preceding embodiments, wherein the test element holder comprises at least one receptacle configured for receiving the test element.

Embodiment 14

The test element analysis system according to the preceding embodiment, wherein the barcode reader and the measuring device are located on opposing sides of the receptacle.

Embodiment 15

The test element analysis system according to any one of the preceding embodiments, wherein the test element analysis system further comprises at least one test element having at least one measuring zone capable of performing at least one change being characteristic for the analyte or the parameter, the test element further having at least one barcode.

Embodiment 16

The test element analysis system according to the preceding embodiment, wherein the test element is an electrochemical test element.

Embodiment 17

The test element analysis system according to any one of the two preceding embodiments, wherein the barcode carries at least one optical information selected from the group consisting of: a type of test; a batch or lot number; a manufacturing date; an expiration date; and an item of information about a calibration.

Embodiment 18

The test element analysis system according to any one of the three preceding embodiments, wherein the test element comprises at least one capillary configured for receiving the sample.

Embodiment 19

The test element analysis system according to any one of the four preceding embodiments, wherein the test element comprises at least one reagent configured for activating a coagulation of components of the body fluid.

Embodiment 20

The test element analysis system according to any one of the preceding embodiments, wherein the electronic control element comprises at least one barcode evaluation device configured for at least one of recording, storing, evaluating, monitoring of optical information provided by the camera.

Embodiment 21

The test element analysis system according to any one of the preceding embodiments, wherein the camera is an integrated camera chip comprising one or more of a CCD or a CMOS camera.

Embodiment 22

The test element analysis system according to the preceding embodiment, wherein the integrated camera chip further comprises one or more of a lens system or an aperture system.

Embodiment 23

The test element analysis system according to any one of the preceding embodiments, wherein the camera carrier element comprises electrical contacts electrically connected to the camera.

Embodiment 24

The test element analysis system according to any one of the preceding embodiments, wherein electrical contacts of the camera carrier element are electrically connected to at least one electrical contact of the circuit board.

Embodiment 25

The test element analysis system according to the preceding embodiment, wherein the electrical contact of the circuit board is located on the reverse side of the circuit board and wherein the circuit board comprises at least one via electrically connecting the electrical contact of the circuit board with the at least one electronic control element disposed on the front side Embodiment 26

A method for manufacturing the test element analysis system according to any one of the preceding embodiments, the method comprising:

a) providing the circuit board;
b) providing the camera carrier element;
c) connecting the camera to the camera carrier element;
d) connecting the camera carrier element to the reverse side of the circuit board.

Embodiment 27

The method according to the preceding embodiment, wherein the camera is connected to the camera carrier element by bonding.

Embodiment 28

The method according to any one of the two preceding embodiments, wherein the camera carrier element is bonded to the reverse side of the circuit board.

Embodiment 29

The method according to any one of embodiments 26 or 27, wherein the camera carrier element and the circuit board are manufactured as one single piece.

Embodiment 30

A barcode reader for reading at least one barcode, wherein the barcode reader comprises:
  at least one circuit board, the circuit board having a front side facing the barcode and at least one reverse side facing away from the barcode, wherein at least one electronic control element of the barcode reader is disposed on the circuit board and wherein the circuit board comprises at least one cavity penetrating the circuit board;
  at least one camera carrier element being disposed on the reverse side of the circuit board;
  at least one camera, the camera being electrically connected to the camera carrier element, with the camera carrier element and the camera being positioned such that the camera observes the barcode through the cavity.

Embodiment 31

The barcode reader according to the preceding embodiment, the barcode reader having the features referring to a barcode reader as disclosed in one or more of embodiments 1 to 25.

In order that the embodiments of the disclosure may be more readily understood, reference is made to the following examples, which are intended to illustrate but not limit the scope thereof.

FIGS. 1A and 1B show an exemplary embodiment of a test element 110 in a back view (FIG. 1A) and in a front view (FIG. 1B). The test element 110 may specifically be a strip-shaped test element 112 and may also be referred to as test strip 114. The test element 110 may specifically be an electrochemical test element 116. The electrochemical test element 116 may be configured for performing at least one electrochemical detection. Therefore, the test element 110 may have at least one measuring zone 118 capable of performing at least one change being characteristic for an analyte or parameter of a sample. An electrical quantity may be measured by means of electrodes (not shown) provided in the measuring zone 118. The test element 110 may comprise electrically conductive contact surfaces 120. An electrical signal may be passed onto the electrically conductive contact surfaces 120 via conductor paths 122. The test element 110 may comprise at least one capillary 124 configured for receiving the sample. The capillary 124 may be configured such that a fluidic medium such as the sample may migrate through the capillary 124 by capillary action. The capillary 124 may comprise at least one inlet 126 and at least one ventilation opening 128.

The test element 110 may further comprise at least one barcode 130 as shown in FIG. 1B. The barcode 130 may be a two-dimensional barcode 132, specifically a data matrix code 134. The barcode 130 may comprise a plurality of modules 136. The modules 136 may exemplarily be embodied as squares or rectangles. Specifically, the barcode 130 may carry at least one optical information selected from the group consisting of: a type of test; a batch or lot number; a manufacturing date; an expiration date; and an item of information about a calibration. Still, other optical information is feasible. The barcode 130 may be configured to be read out by optical or optoelectronic means. Thereby, the modules 136 may be configured to assume at least two different optically detectable states.

FIGS. 2A and 2B show an exemplary embodiment of a camera carrier element 138 in a perspective view (FIG. 2A) and in a front view (FIG. 2B). The camera carrier element 138 may specifically be a printed circuit board 140 and may exemplarily have a rectangular shape. Still, other embodiments are feasible. The camera carrier element 138 may specifically comprise at least one camera carrier element cavity 142. Specifically, the camera carrier element cavity 142 may be a blind hole 144 with an opening 146. The opening 146 may face towards a test element 110, such as the test element 110 as described within FIGS. 1A to 1B, when placed inside a test element holder of an evaluation device. The camera carrier element cavity 142 may have a round cross section. Still, other embodiments are feasible. Further, the camera carrier element 138 may comprise at least one electrical contact pad 148 inside the camera carrier element cavity 142.

Figure 3A:
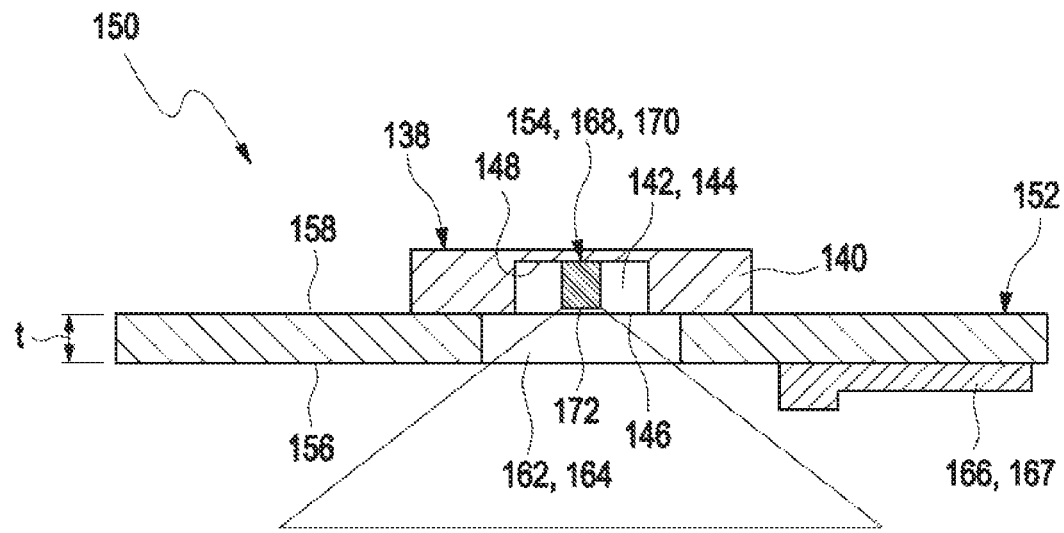
FIG. 3A shows an exemplary embodiment of a bar code reader in a cross-sectional view.
Figure 3B:
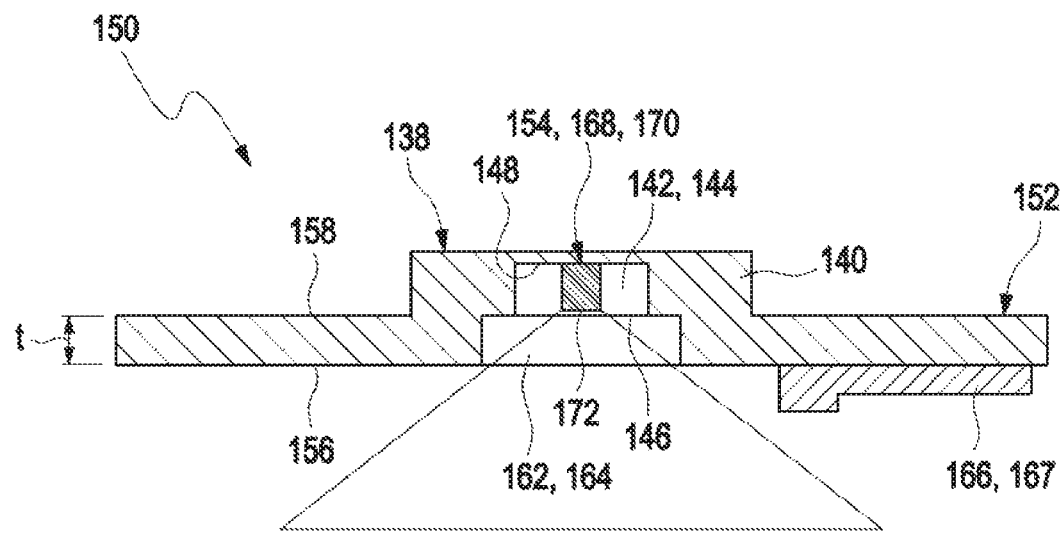
FIG. 3B shows another exemplary embodiment of a bar code reader in a cross-sectional view.

FIGS. 3A and 3B show exemplary embodiments of a barcode reader 150 in cross-sectional views. The barcode reader 150 comprises at least one circuit board 152, at least one camera 154 and at least one camera carrier element 138. The camera carrier element 138 may correspond at least in wide parts to the camera carrier element 138 as illustrated in FIGS. 2A and 2B. Thus, reference may be made to the description of FIGS. 2A and 2B above.

The circuit board 152 has a front side 156 and a reverse side 158. The front side 156 faces the barcode 130 of the test element 110 (not shown in FIGS. 3A, 3B) positioned in a test element holder 160 (not shown in FIGS. 3A, 3B). The reverse side 158 faces away from the test element 110. The circuit board 152 comprises at least one cavity 162. The cavity 162 fully or partially penetrates the circuit board 152. Specifically, the cavity 162 may be a through-hole 164 in the circuit board 152. Exemplarily, the cavity 162 may have a round cross section or a rectangular cross section. Still, other embodiments are feasible. Beyond, the circuit board 152 comprises at least one electronic control element 166 of the barcode reader 150. The electronic control element 166 is disposed on the circuit board 152. The barcode reader 150 may comprise at least one barcode evaluation device 167 configured for at least one of recording, storing, evaluating, monitoring of optical information provided by the camera 154. The barcode evaluation device 167 may be part of the electronic control element 166.

The camera carrier element 138 is disposed on the reverse side 158 of the circuit board 152. Exemplarily, as shown in FIG. 3A, the camera carrier element 138 is bonded onto the reverse side 158 of the circuit board 152. Alternatively, as shown in FIG. 3B, the camera carrier element 138 may be integrated into the reverse side 158 of the circuit board 152.

The camera 154 may be an integrated camera chip 168 exemplarily comprising a CCD camera 170. Further, the integrated camera chip 168 may comprise one or more of a lens system or an aperture system (not shown). The camera 154 is electrically connected to the camera carrier element 138. Specifically, the camera 154 may be electrically bonded onto the electrical contact pad 148 of the camera carrier element 138. The camera carrier element 138 and the camera 154 are positioned such that the camera 154 observes the barcode 130 (not shown in FIGS. 3A, 3B) through the cavity 162 of the circuit board 152. The camera 154 may comprise a front face 172. A distance between the barcode 130 of the test element 110 inside the test element holder 160 and the front side 156 of the circuit board 152 may be smaller or less than a distance between the barcode 130 and the front face 172 of the camera 154. Specifically, the distance between the barcode 130 and the front face 172 of the camera 154 may exceed the distance between the barcode 130 and the front side 156 of the circuit board 152 by at least the thickness t of the circuit board 152. The thickness t of the circuit board 152 may contribute to a free working distance of the camera 154.

Figure 4:
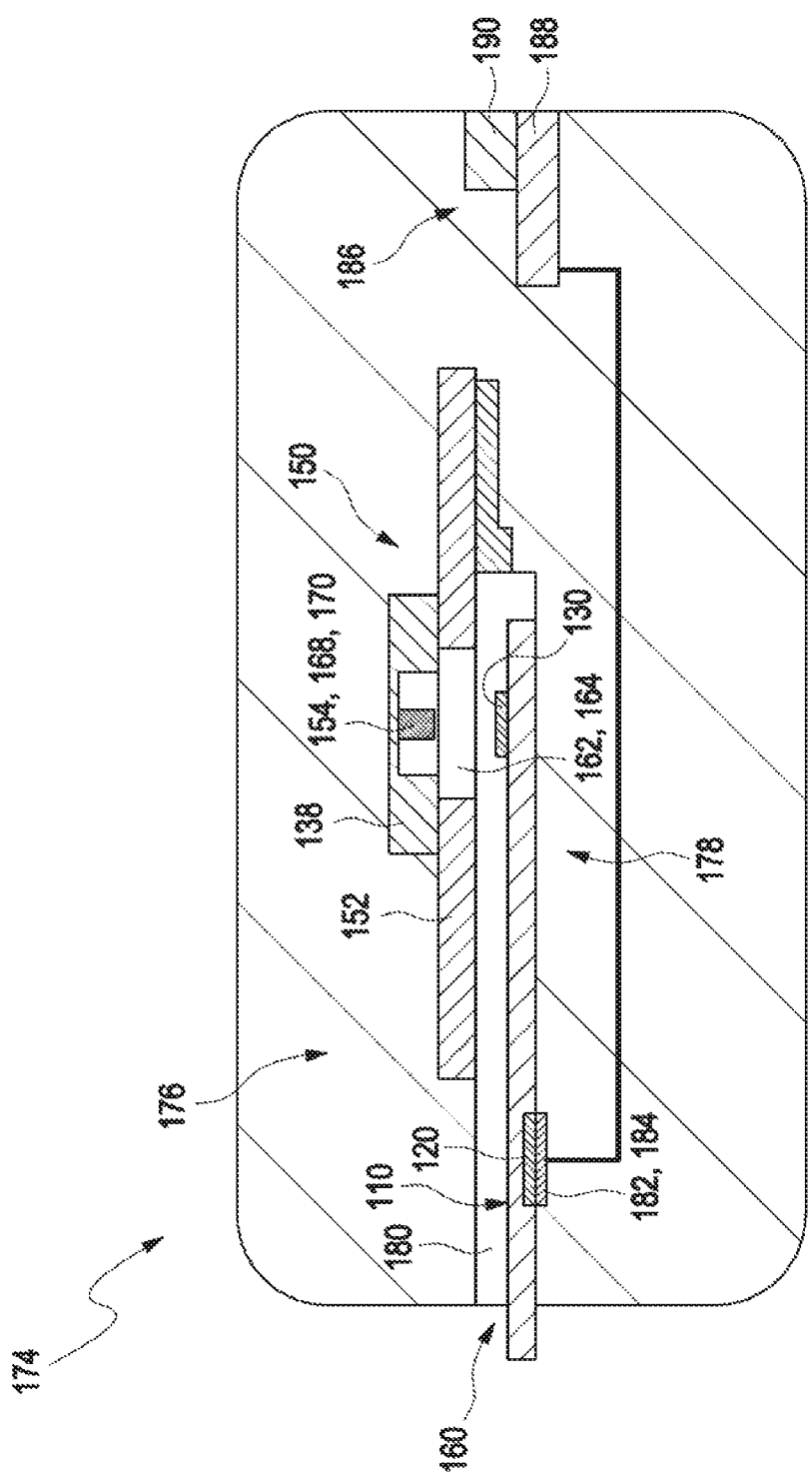
FIG. 4 shows an exemplary embodiment of a test element analysis system in a cross-sectional view.

FIG. 4 shows an exemplary embodiment of a test element analysis system 174 in a cross-sectional view. The test element analysis system 174 is configured for the analytical examination of a sample, in particular of a body fluid. The test element analysis system 174 comprises at least one evaluation device 176 with a test element holder 160 and a measuring device 178. Further, the test element analysis system 174 comprises at least one barcode reader 150. The barcode reader 150 comprises at least one circuit board 152, at least one camera carrier element 138 and at least one camera 154. The barcode reader 150 corresponds at least in wide parts to the barcode reader 150 as illustrated in FIGS. 3A and 3B. Thus, reference may be made to the description of FIGS. 3A and 3B above. The test element 110 may correspond at least in wide parts to the test element 110 as illustrated in FIGS. 1A and 1B. Thus, reference may be made to the description of FIGS. 1A and 1B above.

The test element holder 160 is configured for positioning a test element 110 containing the sample. Therefore, test element holder 160 may comprise at least one receptacle 180 configured for receiving the test element 110. Thus, the receptacle 180 may be shaped complementary to the test element 110. The receptacle 180 and the test element 110 may be configured to establish a form-fit connection. Specifically, the test element 110 may be positioned fixedly on a specific position within the test element holder 160 such that a movement of the test element 110 in at least one direction may be suppressed at least to a large extent. Thus, the measuring zone 118 and/or the barcode 130 of the test element 110 may be located in a predetermined position relative to the measuring device 178 and the camera 154, respectively. Specifically, the barcode reader 150 and the measuring device 178 may be located on opposing sides of the receptacle 180. Still, other embodiments are feasible.

The measuring device 178 is configured for measuring a change in the measuring zone 118 of the test element 110, the change being characteristic for the analyte or the parameter of the sample. The test element holder 160 may comprise contact elements 182 with contact surfaces 184 which may allow an electrical contact between the electrically conductive contact surfaces 120 of the test element 110. The contact element 182 may be connected to measuring and evaluation electronics 186 which may be highly integrated in order to achieve a very compact construction and high degree of reliability. Measuring and evaluation electronics 186 may specifically comprise a printed circuit board 188 and an integrated circuit 190. Still, other embodiments are feasible.

LIST OF REFERENCE NUMBERS 110 test element
112 strip-shaped test element
114 test strip
116 electrochemical test element
118 measuring zone
120 contact surfaces
122 conductor paths
124 capillary
126 inlet
128 ventilation opening
130 barcode
132 two-dimensional barcode
134 data matrix code
136 module
138 camera carrier element
140 printed circuit board
142 camera carrier element cavity
144 blind hole
146 opening
148 electrical contact pad
150 barcode reader
152 circuit board
154 camera
156 front side
158 reverse side
160 test element holder
162 cavity
164 through-hole
166 electronic control element
167 barcode evaluation device
168 integrated camera chip
170 CCD camera
172 front face
174 test element analysis system
176 evaluation device
178 measuring device
180 receptacle
182 contact element
184 contact surface
186 measuring and evaluation electronics
188 printed circuit board
190 integrated circuit

What is claimed is:

1. A test element analysis system for the analytical examination of a sample, comprising:
    at least one evaluation device with at least one test element holder for positioning at least one test element containing the sample and at least one measuring device for measuring a change in a measuring zone of the test element, the change being characteristic for an analyte or a parameter of the sample;
    at least one barcode reader for reading at least one barcode on the test element, wherein the barcode reader comprises:

at least one circuit board, the circuit board having a front side facing the barcode of the test element positioned in the test element holder and at least one reverse side facing away from the test element, wherein at least one electronic control element of the barcode reader is disposed on the circuit board, wherein said electronic control element is configured for one or more of driving, monitoring or evaluating a barcode reading function, and wherein the circuit board comprises at least one cavity penetrating the circuit board;

at least one camera carrier element being disposed on the reverse side of the circuit board; and at least one camera, the camera having a front face facing the barcode, the camera being electrically connected to the camera carrier element, with the camera carrier element and the camera being positioned such that the camera observes the barcode through the cavity without the front face of the camera passing into or through the cavity.

2. The test element analysis system of claim 1, wherein the camera carrier element is one of bonded onto the reverse side of the circuit board, integrated into the reverse side of the circuit board or connected to the reverse side of the circuit board via at least one plug connection.

3. The test element analysis system of claim 1, wherein the camera carrier element comprises at least one printed circuit board having at least one electrical contact pad with the camera electrically bonded thereon.

4. The test element analysis system of claim 1, wherein the circuit board and the camera carrier element are printed circuit boards, and wherein the printed circuit board of the camera carrier element is bonded on the reverse side of the circuit board.

5. The test element analysis system of claim 1, wherein the cavity is a through-hole in the circuit board.

6. The test element analysis system of claim 1, wherein the camera carrier element comprises a camera carrier element cavity, wherein the camera carrier element is positioned such that the camera carrier element cavity is fully or partially located inside the cavity of the circuit board or in an overlapping fashion with the cavity of the circuit board, wherein the camera is mounted inside the camera carrier element cavity.

7. The test element analysis system of claim 6, wherein the camera carrier element comprises at least one electrical contact pad inside the camera carrier element cavity, and wherein the camera is electrically bonded onto the electrical contact pad of the camera carrier element.

8. The test element analysis system of claim 1, wherein the camera comprises a front face, wherein a distance between the barcode of the test element inside the test element holder and the front side of the circuit board is smaller or less than a distance between the barcode and the front face of the camera.

9. The test element analysis system of claim 1, wherein the distance between the barcode and the front face of the camera exceeds the distance between the barcode and the front side of the circuit board by at least the thickness of the circuit board.

10. The test element analysis system of claim 1, wherein the test element holder comprises at least one receptacle configured for receiving the test element, and wherein the barcode reader and the measuring device are located on opposing sides of the receptacle.

11. The test element analysis system of claim 1 further comprising at least one test element having at least one measuring zone configured to perform at least one change being characteristic for the analyte or the parameter of the sample, the test element further comprising at least one barcode.

12. The test element analysis system of claim 1, wherein the barcode carries at least one optical information selected from the group consisting of: a type of test; a batch number; a lot number; a manufacturing date; an expiration date; and an item of information about a calibration.

13. The test element analysis system of claim 1, wherein the barcode reader comprises at least one barcode evaluation device configured for at least one of recording, storing, evaluating, or monitoring of optical information provided by the camera.

14. The test element analysis system of claim 1, wherein the camera carrier element comprises electrical contacts electrically connected to the camera, wherein electrical contacts of the camera carrier element are electrically connected to at least one electrical contact of the circuit board, wherein the electrical contact of the circuit board is located on the reverse side of the circuit board, and wherein the circuit board comprises at least one via electrically connecting the electrical contact of the circuit board with the at least one electronic control element disposed on the front side.

15. The test element analysis system of claim 1, wherein the sample is a body fluid.

* * * * *